United States Patent [19]
Ito

[11] Patent Number: 5,563,290
[45] Date of Patent: Oct. 8, 1996

[54] METHOD FOR PREPARING OPTICALLY ACTIVE SUCCINIC ACID COMPOUND

[75] Inventor: Yoshihiko Ito, Kyoto, Japan

[73] Assignee: Nippon Oil Co. Ltd., Tokyo, Japan

[21] Appl. No.: 367,052

[22] Filed: Dec. 30, 1994

[30] Foreign Application Priority Data

Jan. 12, 1994 [JP] Japan ..................... 6-001530

[51] Int. Cl.$^6$ .................................. C07C 69/34
[52] U.S. Cl. .................. 560/193; 560/146; 560/190; 560/194; 562/592; 562/401
[58] Field of Search ................... 560/146, 194, 560/193, 190; 562/592, 401

[56] References Cited

U.S. PATENT DOCUMENTS 4,142,992  3/1979  Knowles et al. ................. 252/431
4,939,288  7/1990  Talley ................................. 560/81

OTHER PUBLICATIONS

Chemical Abstracts 119:117554, Oct. 8, 1992.

*Primary Examiner*—Samuel Barts
*Attorney, Agent, or Firm*—Darby & Darby, P.C.

[57] ABSTRACT

A method for preparing an optically active succinic acid compound involves hydrogenating an itaconic acid compound in the presence of a rhodium compound and a 2,2"-bis(1-(hydrocarbon residue-substituted) phosphine-substituted alkyl)-1,1"-biferrocene compound.

8 Claims, No Drawings

METHOD FOR PREPARING OPTICALLY ACTIVE SUCCINIC ACID COMPOUND

BACKGROUND OF THE INVENTION

This invention relates to a method for preparing an optically active succinic acid compound such as α- or β-methyl succinic acid and derivatives thereof, which is a reaction intermediate useful for synthesis of a variety of physiologically active materials, such as natural products or pharmaceuticals having an optically active carbon, or functional materials, such as low molecular and high molecular liquid crystal materials.

Natural organic compounds having asymmetric carbon usually exist as an optically active material and exhibit physiological activity markedly different from that of enantiomers. For this reason, investigations into catalytic asymmetric synthesis of natural compounds having asymmetric carbon or artificial compounds having asymmetric carbon are proceeding briskly.

Optically active α-methyl succinic acid can be employed for a variety of fields of application and hence has been prepared by a number of methods. These may be enumerated by a method of optically resolving a racemate produced by reduction of itaconic acid, citraconic acid or mesaconic acid, using quinine or strychnine, as disclosed in, for example, E. Berner and R. Leonardsen, Ann., 538,1 (1939), and a method of asymmetric hydrogenation of itaconic acid using an asymmetric rhodium complex, as disclosed for example in C. Fisher and H. S. Mosher, Tetrahedron Lett., 2487 (1977) and K. Yamamoto, A. Tomita and J. Tsuji, Chem. Lett.,3 (1977).

However, the optical purity of methyl succinic acid produced by these methods is low and amounts only to 52% ee (enantiomer excess) such that the compound can hardly be employed as a starting material for physiologically active materials or functional materials. Although subsequent studies by I. Ojima et al. succeeded in raising the optical purity to the order of 94% ee (I. Ojima, T. Kogure and Y. Yoda, J. Org. Chem., 45,4728 (1980)), the conversion amounts to 94% at most, despite the high hydrogen pressure of 20 atm employed, such that the non-reacted starting material needs to be separated, while hydrogenated products need to be raised in optical purity by some means or other.

SUMMARY OF THE INVENTION

It is an object of the present invention to provide a method for preparing an optically active succinic acid compound such as α- or β-methyl succinic acid or derivatives thereof by catalytic asymmetric hydrogenation of itaconic acid or derivatives thereof, wherein high reactivity and high optical yield can be achieved under relatively moderate conditions.

The above and other objects of the present invention will become clear from the following description.

According to the present invention, there is provided a method for preparing an optically active succinic acid compound comprising hydrogenating an itaconic acid compound in the presence of a rhodium compound and a 2,2"-bis(1-(hydrocarbon residue-substituted) phosphine-substituted alkyl)-1,1"-biferrocene compound selected from the following formulas (I), (II), (III) and (IV):

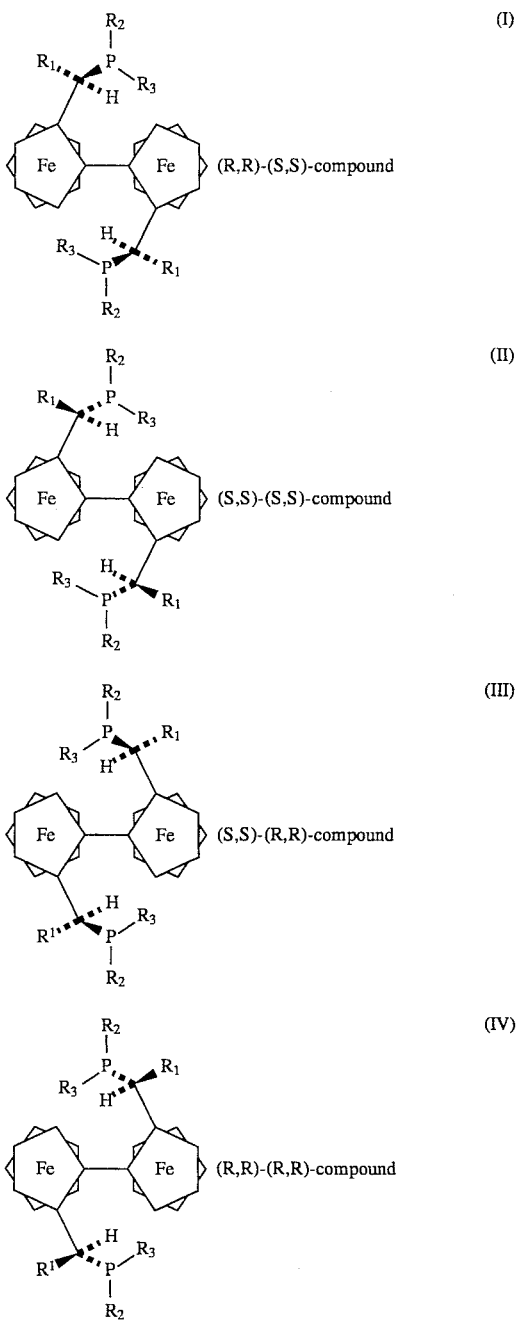

where $R_1$ represents an alkyl group having 1 to 4 carbon atoms, and $R_2$ and $R_3$ each represent an alkyl group having 1 to 4 carbon atoms, a phenyl group, a naphthyl group or a phenyl or naphthyl group substituted with a methyl or ethyl group, the itaconic acid compound being represented by the formula (V)

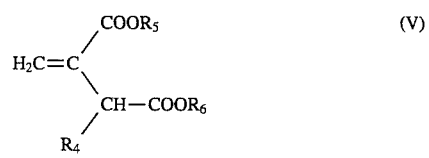

wherein $R_4$ represents a hydrogen atom, a methyl group or an ethyl group, and $R_5$ and $R_6$ may be the same or different and represent a hydrogen atom, an alkyl group having 1 to 6 carbon atoms, a cycloalkyl group or a phenyl group.

PREFERRED EMBODIMENTS OF THE INVENTION

The present invention will be explained hereinbelow in more detail.

With the method according to the present invention, optically active α- or β-methyl succinic acid or derivatives thereof, referred to herein as optically active succinic acid compound, may be produced at extremely high reactivity and hitherto unprecedented high optical yield by hydrogenating itaconic acid or derivatives thereof using, as a catalyst, an optically active 2,2"-bis(1-(hydrocarbon residue-substituted) phosphine-substituted alkyl)-1,1"-biferrocene compound and a rhodium compound in combination.

This high optical yield is ascribable to the optically active 2,2"-bis(1-(hydrocarbon residue-substituted) phosphine-substituted alkyl) 1,1"-biferrocene compound employed, referred to herein briefly as biferrocene compound. The reason is that, when this biferrocene compound coordinates to rhodium, the phosphorus atom is located at the trans position, instead of at the cis position, in distinction from the conventional asymmetric hydrogenation catalyst, and that not only the asymmetry of carbon bonded to the phosphorus atom of the biferrocene compound but also asymmetry attributable to the biferrocene plane is responsible for the optical asymmetry of this biferrocene compound.

The above-mentioned biferrocene compounds employed in the present invention are selected from biferrocene compounds of the formulas (I) to (IV), as described above. In these formulas (I) to (IV), $R_1$ denotes an alkyl group having 1 to 4 carbon atoms, such as methyl, ethyl, propyl, i-propyl, butyl, s-butyl and t-butyl groups, and $R_2$ and $R_3$ may be the same or different and denote C1 to C4 alkyl groups, phenyl groups, naphthyl groups not substituted or substituted by methyl groups or ethyl groups. The groups $R_2$ or $R_3$ may be enumerated by methyl, ethyl, propyl, i-propyl, butyl, s-butyl, t-butyl, phenyl, tolyl, xylyl, mesityl, ethyl phenyl, naphthyl, methyl naphthyl and ethyl naphthyl groups.

While there are a number of optical isomers among the biferrocene compounds, four of these optical isomers, namely a biferrocene compound of the (R,R)-(S,S)-compound, a biferrocene compound of the (S,S)-(S,S)- compound, a biferrocene compound of the (S,S)-(R,R)- compound and a biferrocene compound of the (R,R)-(R,R)-compound, are employed in the method of the present invention.

Specifically, the biferrocene compounds include biferrocene compounds having the configuration of the (R,R)-(S,S), (S,S)-(S,S), (S,S)-(R,R) and (R,R)-(R,R) compounds, and may be enumerated by 2,2"-bis(1-(dimethylphosphino)ethyl)-1,1"-biferrocene, 2,2"-bis(1-(diethylphosphino)ethyl)-1,1"-biferrocene, 2,2"-bis(1-(di-n-propylphosphino)ethyl)-1,1"-biferrocene, 2,2"-bis(1-(diisopropylphosphino)ethyl)-1,1"-biferrocene, 2,2"-bis(1-(di-n-butylphosphino)ethyl)-1,1"-biferrocene, 2,2"-bis(1-(diphenylphosphino)ethyl)-1,1"-biferrocene, 2,2"-bis(1-(di-o-tolylphosphino)ethyl)-1,1"-biferrocene, 2,2"-bis(1-(di-m-tolylphosphino)ethyl)-1,1"-biferrocene, 2,2"-bis(1-(di-p-tolylphosphino) ethyl)-1,1"-biferrocene, 2,2"-bis(1-(di-α-naphthylphosphino)ethyl)-1,1"-biferrocene, 2,2"-bis(1-(di-β-naphthylphosphino)ethyl)-1,1"-biferrocene, 2,2"-bis(1-(dimethylphosphino)n-propyl)-1,1"-biferrocene, 2,2"-bis(1-(diethylphosphino)-n-propyl)-1,1"-biferrocene, 2,2"-bis(1-(di-n-propylphosphino)-n-propyl)-1,1"-biferrocene, 2,2"-bis(1-(diisopropylphosphino)-n-propyl)-1,1"-biferrocene, 2,2"-bis(1-(di-n-butylphosphino)-n-propyl)-1,1"-biferrocene, 2,2"-bis(1-(diphenylphosphino)-n-propyl)-1,1"-biferrocene, 2,2"-bis(1-(di-o-tolylphosphino)-n-propyl)-1,1"-biferrocene, 2,2"-bis(1-(di-m-tolylphosphino)-n-propyl)-1,1"-biferrocene, 2,2"-bis(1-(di-p-tolylphosphino)-n-propyl)-1,1"-biferrocene, 2,2"-bis(1-(di-α-naphthylphosphino)-n-propyl)-1,1"-biferrocene, 2,2"-bis(1-(di-β-naphtylphosphino)-n-propyl)-1,1"-biferrocene, 2,2"-bis(1-(dimethylphosphino)-n-butyl)-1,1"-biferrocene, 2,2"-bis(1-(diethylphosphino)-n-butyl)-1,1"-biferrocene, 2,2"-bis(1-(di-n-propylphosphino)-n-butyl)-1,1"-biferrocene, 2,2"-bis(1-(diisopropylphosphino)-n-butyl)-1,1"-biferrocene, 2,2"-bis(1-(di-n-butylphosphino)-n-butyl)-1,1"-biferrocene, 2,2"-bis(1-(diphenylphosphino)-n-butyl)-1,1"-biferrocene, 2,2"-bis(1-(di-o-tolylphosphino)-n-butyl)-1,1"-biferrocene, 2,2"-bis(1-(di-m-tolylphosphino)-n-butyl)-1,1"-biferrocene, 2,2"-bis(1-(di-p-tolylphosphino)-n-butyl)-1,1"-biferrocene, 2,2"-bis(1-(di-α-naphthylphosphino)-n-butyl)-1,1"-biferrocene, 2,2"-bis(1-(di-β-naphthylphosphino)-n-butyl)-1,1"-biferrocene, 2,2"-bis(1-(dimetylphosphino)isobutyl)-1,1"-biferrocene, 2,2"-bis(1-(diethylphosphino)isobutyl)-1,1"-biferrocene, 2,2"-bis(1-(di-n-propylphosphino)isobutyl)-1,1"-biferrocene, 2,2"-bis(1-(diisopropylphosphino)isobutyl)-1,1"-biferrocene, 2,2"-bis(1-(di-n-butylphosphino)isobutyl)-1,1"-biferrocene, 2,2"-bis(1-(diphenylphosphino)isobutyl)-1,1"-biferrocene, 2,2"-bis(1-(di-o-tolylphosphino)isobutyl)-1,1"-biferrocene, 2,2"-bis(1-(di-m-tolylphosphino)isobutyl)-1,1"-biferrocene, 2,2"-bis(1-(di-p-tolylphosphino)isobutyl)-1,1"-biferrocene, 2,2"-bis(1-(di-α-naphthylphosphino)isobutyl)-1,1"-biferrocene and 2,2"-bis(1-(di-β-naphthylphosphino)isobutyl)-1,1"-biferrocene. The above compounds may be used singly or two or more of the compounds having the same configuration may be used in combination.

The rhodium compounds employed in the present invention are preferably those substantially dissolved in an organic solvent under the co-existence of the biferrocene compounds or those whose reaction products with the biferrocene compounds are dissolved in organic solvents. Examples of these rhodium compounds specifically include rhodium acetate, rhodium acetylacetonate (III), bis(ethylene) acetylacetonato rhodium (I), acetylacetonato (tetraphenyl cyclobutadiene) rhodium (I), (ρ-chlorocyclo pentadienyl) (1,5-cyclooctadiene) rhodium (I), diacetatobis (1,5-cyclooctadiene) dirhodium, diacetatobis (ρ-norbornadiene) dirhodium, dicarbonyl (pentamethyl cyclopentadienyl) rhodium (I), cyclopentadienyl (tetraphenyl cyclobutadiene) rhodium (I), di-μ-chloro-tetra (ρ-ethylene) dirhodium (I), di-μ-chloro tetracarbonyl dirhodium (I), di-μ-chlorotetrakis (cyclooctene) dirhodium (I), di-μ-chlorobis (1,5-cyclooctadiene) dirhodium (I), di-μ-chlorobis (2,3-dimethyl-2-butene) dirhodium (I), di-μ-chlorobis (ρ-tetraphenyl cyclobutadiene) dirhodium (I), di-μ-chlorobis (norbornadiene) dirhodium (I), di-μ-chlorobis (1,5-hexadiene) dirhodium (I), di-μ-bromobis (1,5-cyclooctadiene) dirhodium (I), bis (1,5-cyclooctadiene) diiodido dirhodium (I), dihydroxobis (1,5-cyclooctadiene) dirhodium (I), ρ-2-methallyl-ρ-cyclooctadiene rhodium (I), bis (ethylene) pentamethyl cyclopentadienyl rhodium (I), dicarbonyl acetylacetonato rhodium (I), bis (1,5-cyclooctadiene) rhodium (I) tetrafluoroborate, bis (ethylene) (hexamethyl benzene) rhodium (I) tetrafluoroborate, (1,5-cyclooctadiene) (toluene) rhodium (I) tetrafluoroborate, (1,5-cyclooctadiene) (1,3-dimethyl benzene) rhodium (I) tetrafluoroborate, (1,5-cyclooctadiene) (1,3,5-trimethyl benzene) rhodium (I) tetrafluoroborate, (1,5-cyclooctadiene) (hexamethyl benzene) rhodium (I) tetrafluoroborate, (1,5-cyclooctadiene) bis (acetonitrile) rhodium (I) tetrafluoroborate, norbornadiene (benzene) rhodium (I) tetrafluoroborate, norbornadiene (toluene)

rhodium (I) tetrafluoroborate, norbornadiene (1,3-dimethyl benzene) rhodium (I) tetrafluoroborate, norbornadiene (1,3, 5-trimethyl benzene) rhodium (I) tetrafluoroborate, norbornadiene (hexamethyl benzene) rhodium (I) tetrafluoroborate, norbornadiene (phenol) rhodium (I) tetrafluoroborate, norbornadiene (anisole) rhodium (I) tetrafluoroborate, diacetonitrile (norbornadiene) rhodium (I) tetrafluoroborate, tetrakis (isocyanide) rhodium (I) ion (+1), tetrakis (isocyanated isopropyl) rhodium (I) tetrafluoroborate, tetrakis (isocyanated t-butyl) rhodium (I) tetrafluoroborate, tetra (p-methoxyphenyl isonitrile) rhodium (I) tetrafluoroborate, diamine (cyclooctadiene) rhodium (I) hexafluorophosphate, diamine (norbornadiene) rhodium (I) hexafluorophosphate, di-μ-chlorotetrakis (ρ- allyl) dirhodium (III), di-μ-chlorotetrakis (ρ-1-methylallyl) dirhodium (III), di-μ-chlorotetrakis (ρ-2-methylallyl) dirhodium (III), di-μ-chlorotetrakis (ρ-1-phenylallyl) dirhodium (III), di-μ-chlorobis (pentamethyl cyclopentadienyl) dirhodium (III), dihydridobis (triethyl silyl) pentamethyl cyclopentadienyl rhodium (III), hydrido octaethyl porphyrinate rhodium (III), tris (acetonitrile) pentamethyl cyclopentadienyl rhodium (III) hexafluorophosphate, and dimethyl-di-μ-methylenebis (pentamethyl cyclopentadienyl) dirhodium (IV). Of these rhodium compounds, tetrafluoro borates and hexafluoro phosphates are most preferred. The above rhodium compounds may be used singly or in combination.

Itaconic acid or derivatives thereof employed in the present invention, referred to herein as itaconic acid compound, is the itaconic acid compound represented by the formula (V). In the itaconic acid compound, $R_4$ denotes a hydrogen atom, a methyl group or an ethyl group, and $R_5$, and $R_6$ denote the same or different groups and denote a hydrogen atom, C1 to C6 alkyl groups, cycloalkyl groups or phenyl groups. The alkyl groups and the cycloalkyl groups are exemplified by a methyl group, an ethyl group, a propyl group, an i-propyl group, a butyl group, a s-butyl group and a t-butyl group, and by a cyclopentyl group and a cyclohexyl group, respectively.

The itaconic acid compound may be enumerated by itaconic acid, dimethyl itaconate, diethyl itaconate, methylethyl itaconate, dipropyl itaconate, di-i-propyl itaconate, dibutyl itaconate, dicyclopentyl itaconate, dicyclohexyl itaconate, diphenyl itaconate, α-methyl itaconic acid, dimethyl α-methyl itaconate, diethyl α-methyl itaconic acid, methylethyl α-methyl itaconate, dipropyl α-methyl itaconate, di-i-propyl α-methyl itaconate, dibutyl α-methyl itaconate, dicyclopentyl α-methyl itaconate, dicyclohexyl α-methyl itaconate, diphenyl α-methyl itaconate, α-ethyl itaconic acid, dimethyl α-ethyl itaconate, diethyl α-ethyl itaconate, methylethyl α-ethyl itaconate, diisopropyl α-ethyl itaconate, dicyclopentyl α-ethyl itaconate, dicyclohexyl α-ethyl itaconate and diphenyl α-ethyl itaconate.

In the method of the present invention, the optically active succinic acid compound is produced by hydrogenating the itaconic acid compound in the presence of the biferrocene compound and the rhodium compound, as described above. The produced optically active succinic acid compounds may be enumerated by R-compound or S-compound represented by the following formulas:

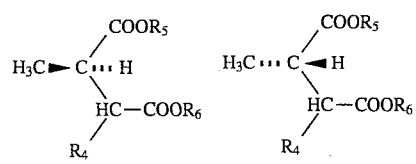

where $R_4$, $R_5$ and $R_6$ are the same as those in the above formula (V). A wide variety of the optically active succinic acid compounds are produced depending on the kinds of the biferrocene compounds and the rhodium compounds used as catalysts. Preferred examples of the optically active succinic acid compounds include α-methyl succinic acid, dimethyl α-methyl succinate, diethyl α-methyl succinate, methylethyl α-methyl succinate, dipropyl α-methyl succinate, di-i-propyl α-methyl succinate, dibutyl α-methyl succinate, dicyclopentyl α-methyl succinate, dicyclohexyl α-methyl succinate, diphenyl α-methyl succinate, α-ethyl β-methyl succinic acid, dimethyl α-ethyl β-methyl succinate, diethyl α-ethyl β-methyl succinate, methylethyl α-ethyl β-methyl succinate, di-i-propyl α-ethyl β-methyl succinate, dicyclopentyl α-ethyl β-methyl succinate, dicyclohexyl α-ethyl β-methyl succinate and diphenyl α-ethyl β-methyl succinate, wherein the respective compounds are R- or S-compounds.

In the method of the present invention, the hydrogenation reaction is carried out usually in the presence of an organic liquid compound, and preferably in the presence of an organic solvent. The hydrogenation reaction is carried out in the presence of the biferrocene compound and the rhodium compound, as described above. Prior to the hydrogenation reaction, the two compounds are preferably dissolved in an organic solvent and contacted or reacted with each other as the occasions may demand. Although there is no limitation to the conditions for such contact or reaction in such case, the contact or the reaction can be usually carried out under the conditions which will permit the compounds to be dissolved and usually for I minute to 1 hour at a temperature of 0° C. to 100° C.

The organic solvents employed in the hydrogenation reaction include any solvents capable of dissolving the biferrocene compounds, rhodium compounds, reaction products of the biferrocene and rhodium compounds and the itaconic acid compound without interfering with the hydrogenation reaction. These solvents include aromatic hydrocarbons, such as benzene, toluene or xylene, ethers such as diethylether, dipropylether, tetrahydrofuran, tetrahydropyran, ethylene glycol dimethylether, or diethylene glycol dimethylether, alcohols, such as methanol, ethanol, isopropanol, ethylene glycol or diethylene glycol, glycol ethers, such as ethylene glycol monomethyl ether or ethylene glycol monoethyl ether, halogenated hydrocarbons, such as methylene chloride, dichloroethane or chlorobenzene, and halohydrins, such as ethylene chlorohydrin or propylene chlorohydrin. These solvents may be used either singly or in combination. There is no necessity of using the solvent in an excess quantity since it suffices to use the solvents in such amounts as will dissolve the catalyst and the itaconic acid compound employed.

In the method of the present invention, it is preferred to carry out the hydrogenation reaction under an inert gas atmosphere, as a principle, and to set the reaction conditions usually of −20° C. to 120° C. and preferably of 0° to 115° C. More specifically, the hydrogenation reaction proceeds smoothly at about room temperature and the desired product may be yielded at substantially the quantitative yield. However, the optical yield may be improved by carrying out the hydrogenation reaction at a temperature higher than the room temperature and closer to the boiling point of benzene, depending on other reaction conditions employed. There is no limitation to the pressure employed for the hydrogenation reaction and the hydrogenation reaction may be carried out usually at a pressure lower than the atmospheric pressure to 50 atm and preferably from 1 to 10 atm. There is no necessity of employing pure hydrogen for the hydrogenation reaction such that it is possible for any gases not obstructing the hydrogenation reaction to exist together with hydrogen. These gases may be nitrogen, helium or argon. If these gases exist together, the hydrogen concentration is preferably 10 mol % or higher.

In the method of the present invention, extremely small charging quantities of the biferrocene compound and the rhodium compound, which are catalysts, may suffice, since the catalyst is highly reactive. Specifically, a quantity of the rhodium compound of preferably 0.01 to 10 mol % and more preferably 0.1 to 1 mol % may be enough with respect to the itaconic acid compound as a substrate, while an equimolar quantity or more of the biferrocene compound with respect to the rhodium compound is preferred. Usually, up to 1000 mole-folds of the biferrocene compound with respect to the rhodium compound may be employed. However, since the biferrocene compound is costly, it is not economically meritorious to use the compound in an excess quantity.

The hydrogenation reaction may be carried out in a batch or semi-batch type reactor or alternatively a continuous type reactor. Although the method of continuously adding only hydrogen by the semi-batch process is customary, the reaction may also be carried out as the substrate is added along with hydrogen. As the continuous method, a tubular type reaction method or the continuous stirred tank reactor type reaction method may be employed. Since the reactivity cannot be raised to 100% with any of these two continuous methods, the product needs to be separated from the starting material. The desired optically active succinic acid compound may be obtained by carrying out post-processing as conventionally after the end of the hydrogenation reaction.

In the method of the present invention, since the itaconic acid compound is processed by an asymmetric hydrogenation reaction using a catalyst comprising the optically active 2,2"-bis(1-(hydrocarbon residue-substituted) phosphine-substituted alkyl)-1,1"-biferrocene compound and the rhodium compound combined together, the optically active succinic acid compound can be produced with an extremely high optical yield. Since an opposite enantiomer need not be isolated from the resulting product, or is yielded in an extremely small quantity, a desired enantiomer can be isolated easily to produce high-purity optically active succinic acid compound.

EXAMPLES OF THE INVENTION

The present invention will be explained in more detail with reference to several illustrative Examples.

EXAMPLE 1

0.0050 mmol of bis (1,5-cyclooctadiene) rhodium (I) tetrafluoroborate and 0.0055 mmol of a (R,R)-(S,S) compound of 2,2"-bis(1-(diethylposphino)ethyl)-1,1"-biferrocene were charged into a 20 ml capacity Schlenk tube fitted with a magnetic rotor, a septum and a reflux condenser fitted with a three-way cock. After the atmosphere in the tube was sufficiently replaced by an argon gas, 1 ml of methylene chloride dried by carrying out freezing and evacuation three times in advance, was added by a syringe and agitated for ten minutes for completely dissolving the catalyst component. 2.50 mmol of dimethyl itaconate as the substrate dried by carrying out freezing and evacuation three times in advance, was dissolved in 1.5 ml of methylene chloride, and then added to the catalyst component system dissolved in the methylene chloride in a reaction vessel, which was cooled with liquid nitrogen and evacuated by a vacuum pump for sufficient evacuation. The temperature was then raised to room temperature. The hydrogen gas was added and the reaction was continued for 30 hours as the hydrogen pressure of 1 atmospheric pressure (absolute) was maintained in a constant temperature vessel of 42° to 45° C. After the end of the reaction, the solvent was distilled off at an atmospheric pressure and distillation was then carried out under reduced pressure. Dimethyl 2-methyl succinate was obtained substantially quantitatively at boiling point of 80° to 90° C. (16 to 24 mmHg). Dimethyl 2-methyl succinate was of the R-type and had a purity of 97% ee (enantiomer excess). The optical purity was determined using HPLC with a CHIRACEL OO-H as a column and a UV absorbing type detector at a wavelength of 230 nm at a flow rate of 0.5 ml/min with hexane/isopropyl alcohol of 9/1.

EXAMPLE 2

The reaction was carried out in the same way as in Example 1 except that the quantity of bis (1,5-cyclooctadiene) rhodium (I) tetrafluoroborate was set to 0.00125 mmol and the quantity of 2,2"-bis(1-(diethyl phosphino)ethyl)-1,1"-biferrocene of (R,R)-(S,S) compound was set to 0.0014 mmol, with the reaction time duration of 72 hours. The results of analyses have indicated that dimethyl 2-methyl succinate of the R-compound having the optical purity of 95% ee was produced.

EXAMPLE 3

0.0055 mmol of bis (1,5-cyclooctadiene) rhodium (I) tetrafluoroborate and 0.0055 mmol of a (R,R)-(S,S) compound of 2,2"-bis(1-(diethylposphino)ethyl)-1,1"-biferrocene were charged into a Schlenk tube, and after the atmosphere in the inside of the tube was sufficiently replaced by an argon gas, 1 ml of methylene chloride dried on calcium hydride was added and agitated for 10 minutes for completely dissolving the catalyst component. 1 mmol of the substrate dimethyl itaconate was added and the tube was cooled to −78° C. After sufficient evacuation using a vacuum pump, the temperature within the tube was raised as the hydrogen gas was added. The reaction was carried out for 24 hours at a constant temperature of 30° C. as the hydrogen pressure of 1 atom (absolute) was maintained. After the end of the reaction, the solvent was distilled off at atmospheric pressure and post-processing was carried out by distillation under reduced pressure. Dimethyl 2-methyl succinate could be produced substantially quantitatively at a boiling point of 80° to 90° C. (16 to 24 mmHg). Dimethyl 2-methyl succinate produced was the R-compound and had the optical purity of 96% ee.

EXAMPLE 4

The reaction was carried out in the same way as in Example 3 except that 2,2"-bis(1-(diethylphosphino)ethyl)-1,1"-biferrocene of the (R,R)-(S,S)-compound was replaced by 2,2"-bis(1-(diethylphosphino)ethyl)-1,1"-biferrocene of the (S,S)-(R,R)-compound. Dimethyl 2-methyl succinate of the S-compound could be produced substantially quantitatively after post-processing with the optical purity of 95% ee.

EXAMPLE 5

The reaction was carried out in the same way as in Example 3 except that the reaction temperature of 70° C. was used. The optical purity of dimethyl 2-methyl succinate of the R-compound produced in this manner was surprisingly as high as 98% ee.

EXAMPLE 6

The reaction was carried out in the same way as in Example 3 except using di-μ-chlorobis (norbornadiene) dirhodium (I) instead of the rhodium compound used in Example 3. After post-processing dimethyl 2-methyl succinate of the R-compound was yielded at a yield of 65%. The optical purity was 85% ee.

EXAMPLE 7

The reaction was carried out in the same way as in Example 3 except using rhodium dicarbonyl acetyl acetonate in place of the rhodium compound used in Example 3. The reaction yielded dimethyl 2-methyl succinate of the R-compound at a yield of 60% with the optical purity of 75% ee.

EXAMPLE 8

A reagent in an amount five times as much as that of Example 3 was charged into an autoclave with a capacity of 50 ml fitted with an agitator, and the processing operation just before addition of the hydrogen gas was carried out similarly as in Example 3. The hydrogen gas was then added up to 50 atm and the reaction was carried out at 30° C. for 24 hours. After the end of the reaction, the residual hydrogen gas was removed and post-processing was carried out in the same way as in Example 3. The results of analyses indicated that the reaction proceeded 100% yield. The optical purity of dimethyl 2-methyl succinate of the R-compound was 60% ee.

EXAMPLE 9

The reaction was carried out in the same way as in Example 3 except using 2,2"-bis(1-(diphenylphosphino)ethyl)-1,1"-biferrocene of the (R,R)-(S,S) compound in place of the biferrocene compound used in Example 3. The reaction yielded dimethyl 2-methyl succinate of the R-compound substantially quantitatively with the optical purity of 92% ee.

EXAMPLE 10

The reaction was carried out in the same way as in Example 3 except using diisopropyl itaconate in place of dimethyl itaconate. The yield of the hydrogenation reaction was 92%, and the optical purity of diisopropyl 2-methyl succinate of the R-compoundd produced was 94% ee.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A method for preparing an optically active succinic acid compound selected from the group consisting of (R)-compound and (S)-compound represented by the formulas:

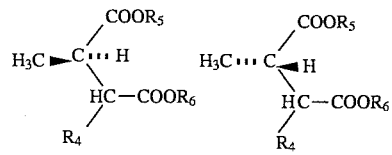

wherein $R_4$ represents a hydrogen atom, a methyl group or an ethyl group, and $R_5$ and $R_6$ may be the same or different and represent a hydrogen atom, an alkyl group having 1 to 6 carbon atoms, a cycloalkyl group or a phenyl group, said method comprising hydrogenating an itaconic acid compound in the presence of a rhodium compound and a 2,2"-bis(1-(alkyl substituted) phosphine-substituted alkyl)-1,1"-biferrocene compound selected from formulas (I), (11), (111), and (IV):

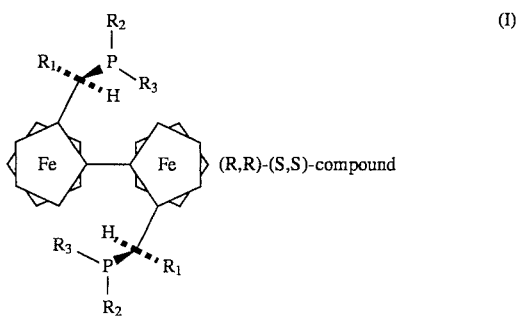
(I) (R,R)-(S,S)-compound

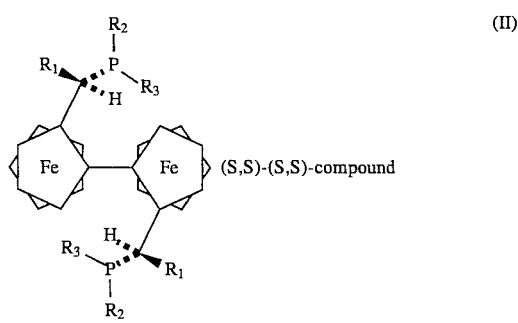
(II) (S,S)-(S,S)-compound

-continued

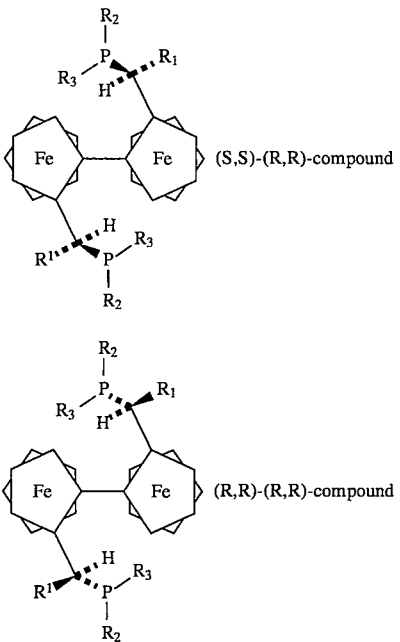

(III) (S,S)-(R,R)-compound (IV) (R,R)-(R,R)-compound where $R_1$, $R_2$ and $R_3$ each represent an alkyl group having 1 to 4 carbon atoms, said itaconic acid compound being represented by the formula (V):

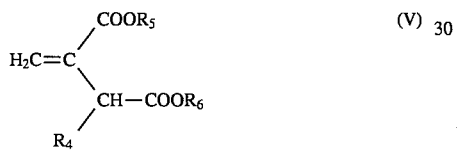

(V)

wherein $R_4$, $R_5$ and $R_6$ are the same as defined in the formulas of said (R)-compound or said (S)-compound.

2. The method as claimed in claim 1 wherein said 2,2"-bis(1-(alkyl-substituted) phosphine-substituted alkyl)-1,1"-biferrocene compound is selected from the group consisting of 2,2"-bis(1-(dimethylphosphino)ethyl)-1, 1"-biferrocene, 2,2"-bis(1-(diethylphosphino)ethyl)-1,1"-biferrocene, 2,2"-bis(1-(di-n-propylphosphino)ethyl)-1,1"-biferrocene, 2,2"-bis(1-(diisopropylphosphino)ethyl)-1,1"-biferrocene, 2,2"-bis(1-(di-n-butylphosphino)ethyl)-1,1"-biferrocene, 2,2"-bis(1-(dimethylphosphino)n-propyl)-1,1"-biferrocene, 2,2"-bis(1-(diethylphosphino)on-propyl)-1,1"-biferrocene, 2,2"-bis(1-(di-n-propylphosphino)-n-propyl)-1, 1"-biferrocene, 2,2"-bis(1-(diisopropylphosphino)-n-propyl)-1,1"-biferrocene, 2,2"-bis(1-(di-n-butylphosphino)-n-propyl)-1,1"-biferrocene, 2,2"-bis(1-(dimethylphosphino)-n-butyl)-1,1"-biferrocene, 2,2"-bis(1-(diethylphosphino)-n-butyl)-1,1"-biferrocene, 2,2"-bis(1-(di-n-propylphosphino)-n-butyl)-1,1"-biferrocene, 2,2"-bis(1-(diisopropylphosphino)-n-butyl)-1,1"-biferrocene, 2,2"-bis(1-(di-n-butylphosphino)-n-butyl)-1,1"-biferrocene, 2,2"-bis(1-(dimethylphosphino)isobutyl)-1,1"-biferrocene, 2,2"-bis(1-(diethylphosphino)isobutyl)-1,1"-biferrocene, 2,2"-bis(1-(di-n-propylphosphino)isobutyl)-1,1"-biferrocene, 2,2"-bis(1-(diisopropylphosphino)isobutyl)-1,1"-biferrocene, 2,2"-bis(1-(di-n-butylphosphino)isobutyl)-1,1"-biferrocene, and mixtures thereof.

3. The method as claimed in claim 1 wherein said rhodium compound is selected from the group consisting of rhodium acetate, rhodium acetylacetonate (III), bis(ethylene) acetylacetonato rhodium (I), acetylacetonato (tetraphenyl cyclobutadiene) rhodium (I), (p-chlorocyclo pentadienyl) (1,5-cyclooctadiene) rhodium (I), diacetatobis (1,5-cyclooctadiene) dirhodium, diacetatobis (ρ-norbornadiene) dirhodium, dicarbonyl (pentamethyl cyclopentadienyl) rhodium (I), cyclopentadienyl (tetraphenyl cyclobutadiene) rhodium (I), di-μ-chloro-tetra (ρ-ethylene) dirhodium (I), di-μ-chloro tetracarbonyl dirhodium (I), di-μ-chlorotetrakis (cyclooctene) dirhodium (I), di-μ-chlorobis (1,5-cyclooctadiene) dirhodium (I), di-μ-chlorobis (2,3-dimethyl-2-butene) dirhodium (I), di-μ-chlorobis (ρ-tetraphenyl cyclobutene) dirhodium (I), di-μ-chlorobis (norbornadiene) dirhodium (I), di-μ-chlorobis (1,5-hexadiene) dirhodium (I), di-μ-bromobis (1,5-cyclooctadiene) dirhodium (I), bis (1,5-cyclooctadiene) diiodido dirhodium (I), dihrdroxobis (1,5-cyclooctadiene) dirhodium (I), ρ-2-methallyl-ρ-cyclooctadiene rhodium (I), bis (ethylene) pentamethyl cyclopentadienyl rhodium (I), dicarbonyl acetylacetonato rhodium (I), bis (1,5-cyclooctadiene) rhodium (I) tetrafluoroborate, bis (ethylene) (hexamethyl benzene) rhodium (I) tetrafluoroborate, (1,5-cyclooctadiene) (toluene) rhodium (I) tetrafluoroborate, (1,5-cyclooctadiene) (1,3-dimethyl benzene) rhodium (I) tetrafluoroborate, (1,5-cyclooctadiene) (1,3,5-trimethyl benzene) rhodium (I) tetrafluoroborate, (1,5-cyclooctadiene) (hexamethyl benzene) rhodium (I) tetrafluoroborate, (1,5-cyclooctadiene) bis (acetonitrile) rhodium (I) tetrafluoroborate, norbornadiene (benzene) rhodium tetrafluoroborate, norbornadiene (toluene) rhodium (i) tetrafluoroborate, norbornadiene (1,3-dimethyl benzene) rhodium (I) tetrafluoroborate, norbornadiene (1,3,5-trimethyl benzene) rhodium (I) tetrafluoroborate, norbornadiene (hexamethyl benzene) rhodium (I) tetrafluoroborate, norbornadiene (phenol) rhodium (I) tetrafluoroborate, norbornadiene (anisole) rhodium (I) tetrafluoroborate, diacetonitrile (norbornadiene) rhodium (I) tetrafluoroborate, tetrakis (isocyanide) rhodium (I) ion (+1), tetrakis (isocyanated isopropyl) rhodium (I) tetrafluoroborate, tetrakis (isocyanated t-butyl) rhodium (I) tetrafluoroborate, tetra (p-methoxyphenyl isonitrile) rhodium (I) tetrafluoroborate, diamine (cyclooctadiene) rhodium (I) hexafluorophosphate, diamine (norbornadiene) rhodium (I) hexafluorophosphate, di-μ-chlorotetrakis (ρ-allyl) dirhodium (III), di-μ-chlorotetrakis (ρ-1-methylallyl) dirhodium (III), di-μ-chlorotetrakis (ρ-2-methylallyl) dirhodium (III), di-μ-chlorotetrakis (ρ-1-phenylallyl) dirhodium (III), di-μ-chlorobis (pentamethyl cyclopentadienyl) dirhodium (III), dihydridobis (triethyl silyl) pentamethyl cyclopentadienyl rhodium (III), hydrido octaethyl porphyrinate rhodium (III), tris (acetonitrile) pentamethyl cyclopentadienyl rhodium (III) hexafluorophosphate, dimethyl-di-μ-methylenebis (pentamethyl cyclopentadienyl) dirhodium (IV), and mixtures thereof.

4. The method as claimed in claim 1 wherein said itaconic acid compound is selected from the group consisting of itaconic acid, dimethyl itaconate, diethyl itaconate, methylethyl itaconate, dipropyl itaconate, di-i-propyl itaconate, dibutyl itaconate, dicyclopentyl itaconate, dicyclohexyl itaconate, diphenyl itaconate, α-methyl itaconic acid, dimethyl α-methyl itaconate, diethyl α-methyl itaconate, methylethyl α-methyl itaconate, dipropyl α-methyl itaconate, di-i-propyl α-methyl itaconate, dibutyl α-methyl itaconate, dicyclopentyl α-methyl itaconate, dicyclohexyl α-methyl itaconate, diphenyl α-methyl itaconate, α-ethyl itaconic acid, dimethyl α-ethyl itaconate, diethyl α-ethyl itaconate, methylethyl α-ethyl itaconate, diisopropyl α-ethyl itaconate, dicyclopentyl α-ethyl itaconate, dicyclohexyl α-ethyl itaconate, diphenyl α-ethyl itaconate, and mixtures thereof.

5. The method as claimed in claim 4 wherein said optically active succinic acid compound is selected from the group consisting of α-methyl succinic acid, dimethyl α-methyl succinate, diethyl α-methyl succinate, methylethyl α-methyl succinate, dipropyl α-methyl succinate, di-i-propyl α-methyl succinate, dibutyl α-methyl succinate, dicyclopentyl α-methyl succinate, dicyclohexyl α-methyl succinate, diphenyl α-methyl succinate, α-ethyl β-methyl succinic acid, dimethyl α-ethyl β-methyl succinate, diethyl α-ethyl β-methyl succinate, methylethyl α-ethyl β-methyl succinate, di-i-propyl b-ethyl β-methyl succinate, dicyclopentyl α-ethyl β-methyl succinate, dicyclohexyl b-ethyl β-methyl succinate, diphenyl α-ethyl β-methyl succinate, and mixtures thereof.

6. The method as claimed in claim 1 wherein, prior to hydrogenation of the itaconic acid compound, said 2,2"-bis(1-(alkyl substituted) phosphine-substituted alkyl)-1,1"-biferrocene compound and said rhodium compound are dissolved in an organic solvent and contacted with each other at 0° C. to 100° C. for one minute to one hour.

7. The method as claimed in claim 1 wherein said itaconic acid compound is hydrogenated in the presence of an inert gas at −20° C. to 120° C. under 1 to 50 atm at a hydrogen concentration of not less than 10 mol %.

8. The method as claimed in claim 1 wherein the rhodium compound is present in an amount of 0.01 to 10 mol % with respect to the itaconic acid compound and wherein said 2,2"-bis(1-(alkyl substituted) phosphine-substituted alkyl)-1,1-biferrocene compound is present in an equal mole to 1000 mole-folds relative to said rhodium compound.

* * * * *